(12) United States Patent
Narawa et al.

(10) Patent No.: US 6,306,122 B1
(45) Date of Patent: Oct. 23, 2001

(54) DISPOSABLE WEARING ARTICLE

(75) Inventors: Mika Narawa; Yoshinobu Machida; Shinobu Takei; Harumitsu Toyoda; Ken Nemoto, all of Tochigi-ken (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/063,046

(22) Filed: Apr. 21, 1998

(30) Foreign Application Priority Data

Apr. 21, 1997 (JP) .................................................. 9-103099

(51) Int. Cl.$^7$ ............................. A61F 13/15; A61F 13/20
(52) U.S. Cl. ........................... 604/385.3; 604/385.01; 604/385.24; 604/385.26; 604/385.27; 604/385.29
(58) Field of Search .................... 604/385.1, 393, 604/385.29, 385.3, 385.31

(56) References Cited

U.S. PATENT DOCUMENTS

| | | | | |
|---|---|---|---|---|
| H1420 | * | 2/1995 | Richardson | 604/385.2 |
| 5,366,453 | * | 11/1994 | Zehner et al. | 604/385.2 |
| 5,916,206 | * | 6/1999 | Otsubo et al. | |

FOREIGN PATENT DOCUMENTS 0623330A 9/1994 (EP).
93/21877A 11/1993 (WO).

OTHER PUBLICATIONS

Patent Abstract of Japan, vol. 015, No. 512 (C–0898), Oct. 3, 1991, DISPOSABLE WEARING ARTICLE.

* cited by examiner

*Primary Examiner*—John G. Weiss
*Assistant Examiner*—Michele Kidwell
(74) *Attorney, Agent, or Firm*—Birch, Stewart, Kolasch & Birch, LLP

(57) ABSTRACT

A disposable wearing article including a liquid-permeable topsheet, an outermost layer sheet located on an outer surface of the disposable wearing article, and a liquid retentive absorbent member, a waist-surrounding elastic member being arranged at a waist-surrounding portion, wherein the waist-surrounding elastic member is fixed to other members than the outermost layer sheet in an expanded state to thereby form gathers inwardly of the outermost layer sheet, a non-bonding area is provided between the waist-surrounding elastic member and the outermost layer sheet, and no gathers are formed on an outer surface of the waist-surrounding portion.

9 Claims, 14 Drawing Sheets

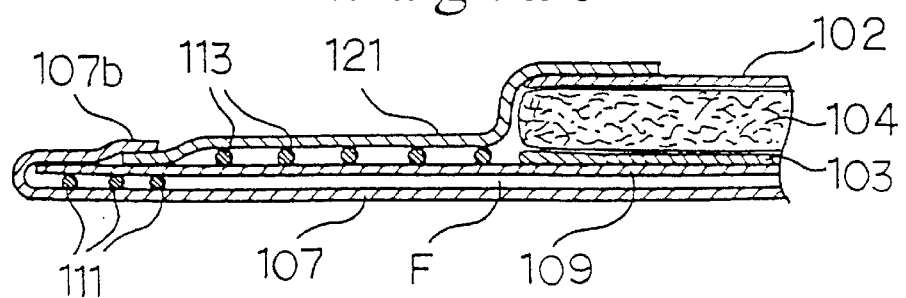
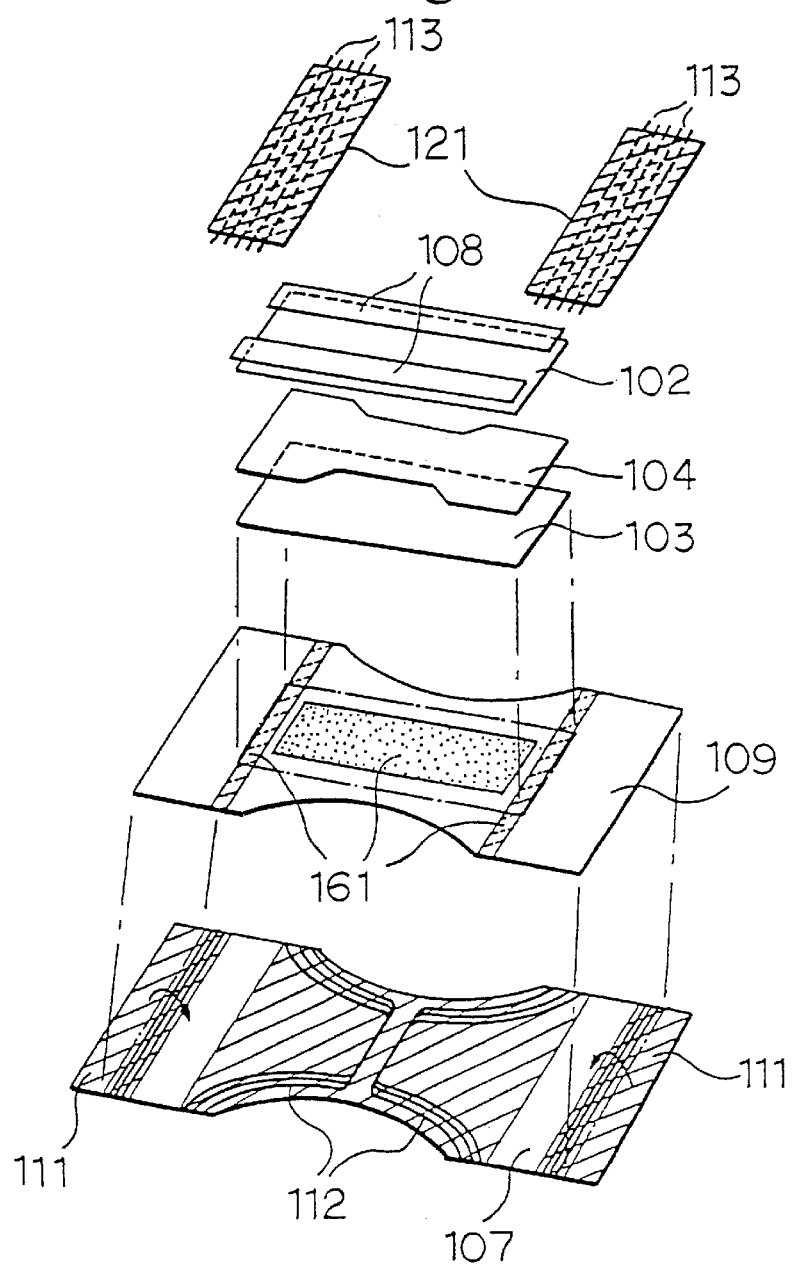

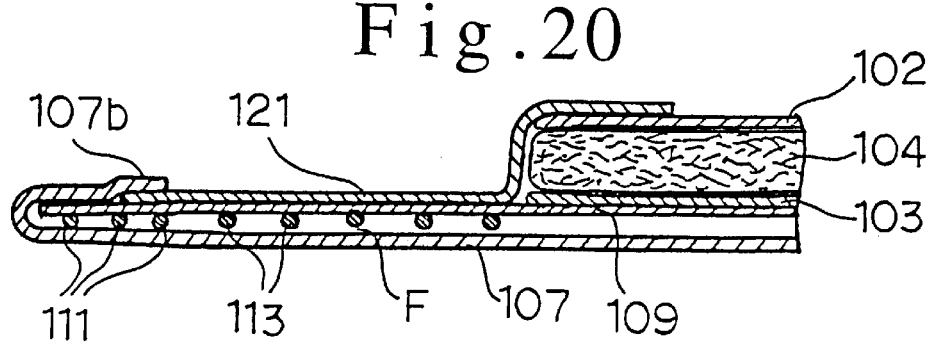
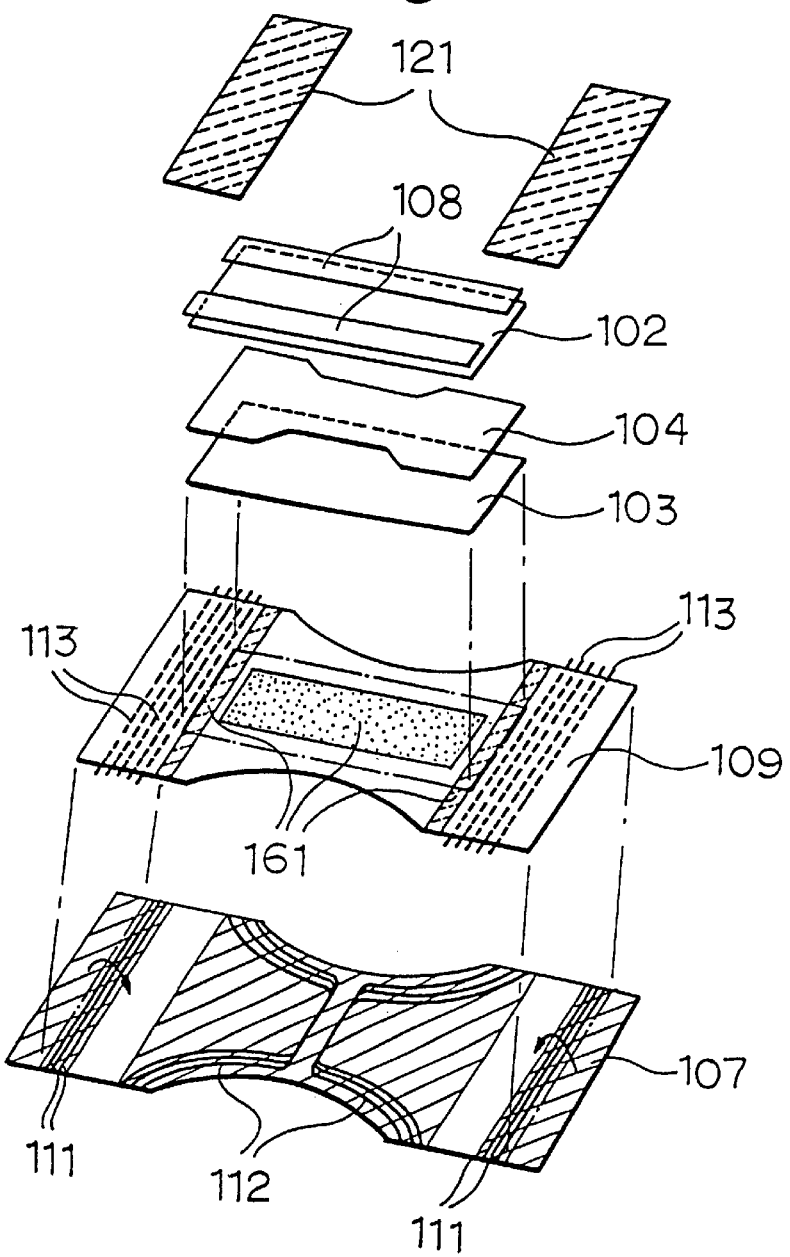

DISPOSABLE WEARING ARTICLE

FIELD OF THE INVENTION

This invention relates to a disposable wearing article such as a disposable diaper, a sanitary napkin, or the like which is not only excellent in outer appearance but also in fitness.

DESCRIPTION OF THE RELATED ART

As a disposable diaper, there has heretofore been widely used a diaper of the type comprising a liquid-permeable topsheet, a liquid-impermeable backsheet, and an absorbent member interposed therebetween, a waist portion elastic member being arranged at a waist portion which is, when in wear, located at its wearer's waist area, a leg portion elastic member being arranged at each leg portion which is, when in wear, located circumferentially around its wearer's leg, and a waist-surrounding elastic member arranged at a waist-surrounding portion which is, when in wear, located at the wearer's waist surrounding area.

In such a disposable diaper, the waist-surrounding elastic member is a member, which is employed in order to enhance fitness to the area circumferentially around the wear's waist, to thereby enhance fitness when in wear. Usually, the waist-surrounding elastic member is bonded to the backsheet such that gathers are formed on an outer surface of the diaper.

For this reason, in the conventional disposable diaper having the waistsurrounding elastic member, it gives rise to such a problem that the gathers deteriorate the outer appearance of the diaper.

SUMMARY OF THE INVENTION

It is, therefore, an object of the present invention to provide a disposable wearing article which is excellent in fitness when in wear and also excellent in outer appearance.

As a result of extensive search and development carried out by the present inventors, they found that the above-mentioned object could be achieved by a disposable wearing article in which a waist-surrounding elastic member is arranged without being bonded to the outermost layer sheet.

The present invention has been accomplished based on the above-mentioned finding, and it provides a disposable wearing article including a liquid-permeable topsheet, an outermost layer sheet located on an outer surface of the disposable wearing article, and a liquid retentive absorbent member, a waist-surrounding elastic member being arranged at a waist-surrounding portion, wherein the waist-surrounding elastic member is fixed to members other than the outermost layer sheet in an expanded state to thereby form gathers inwardly of the outermost sheet, a non-bonding area is provided between the waist-surrounding elastic member and the outermost layer sheet, and no gathers are formed on an outer surface of the waist-surrounding portion.

A disposable wearing article of the present invention is excellent in fitness when in wear, and also excellent in outer appearance.

BRIEF DESCRIPTION OF THE DRAWINGS

FIG. 16 is a schematic longitudinal sectional view (corresponding to FIG. 12) showing the seventh embodiment of the present invention;

FIG. 17 is an exploded perspective view (corresponding to FIG. 13) of the disposable diaper of FIG. 16;

FIG. 20 is a schematic longitudinal sectional view (corresponding to FIG. 12) showing the ninth embodiment of the present invention;

FIG. 21 is an exploded perspective view (corresponding to FIG. 13) of the disposable diaper of FIG. 20;

DESCRIPTION OF THE PREFERRED EMBODIMENTS

One preferred embodiment of a disposable wearing article of the present invention will be described hereinafter with reference to the drawings. The first embodiment of a disposable diaper as the disposable wearing article of the present invention will be described first with reference to FIGS. 1 to 7.

Figure 1:
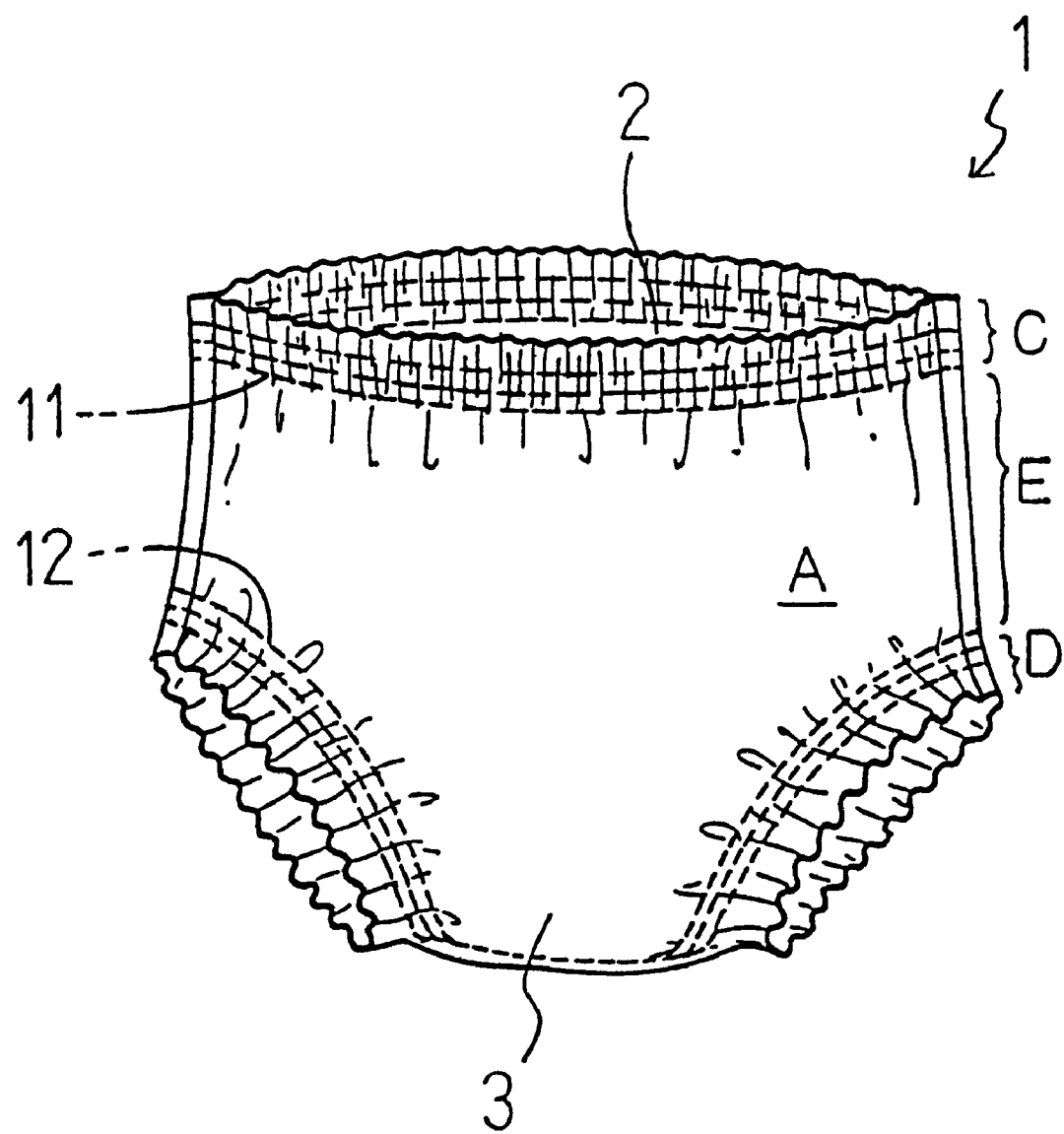
FIG. 1 is a front view showing a disposable diaper as the first embodiment of a disposable wearing article according to the present invention.
Figure 2:
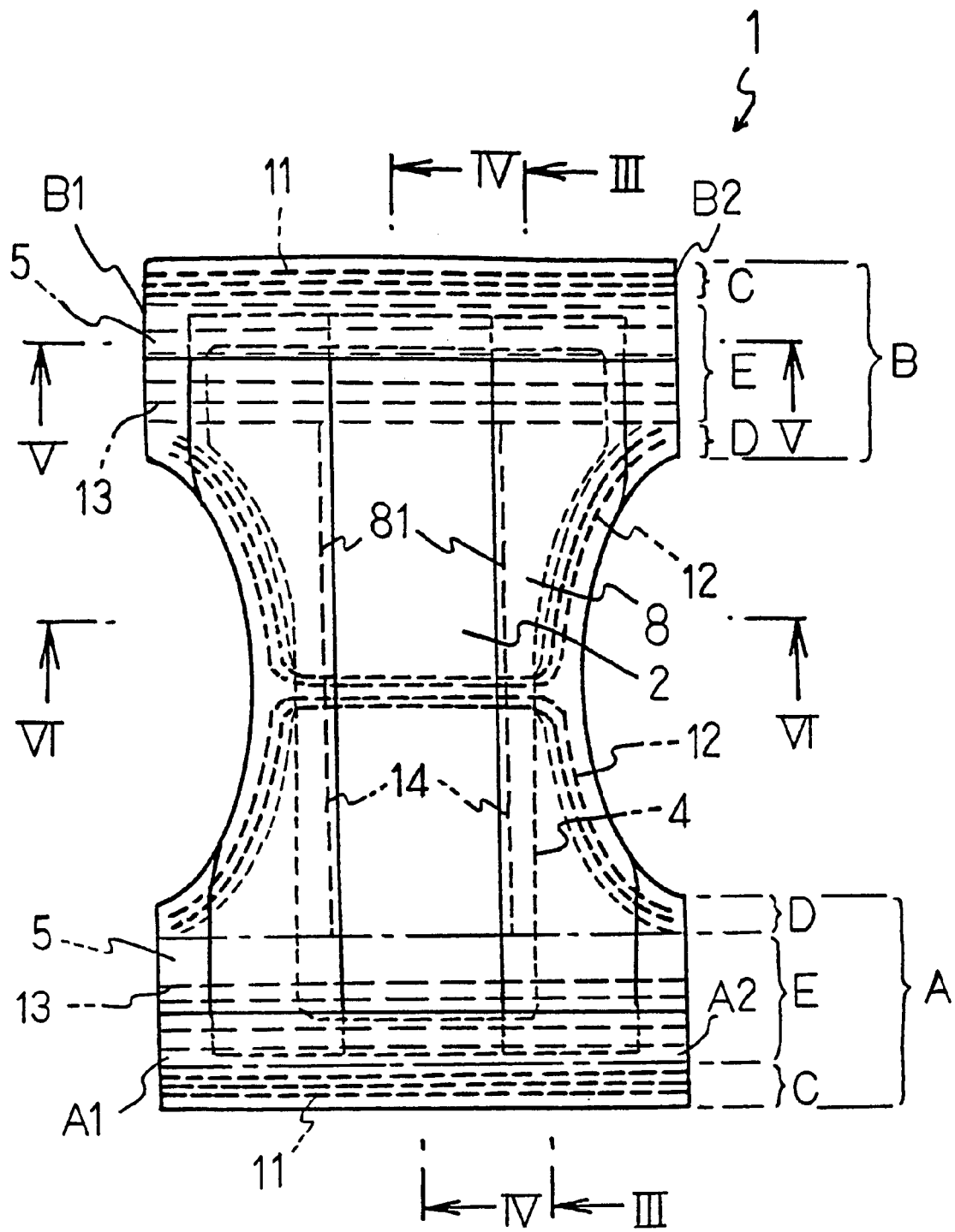
FIG. 2 is a developed view of the disposable diaper of the preferred embodiment of FIG. 1.
Figure 3:
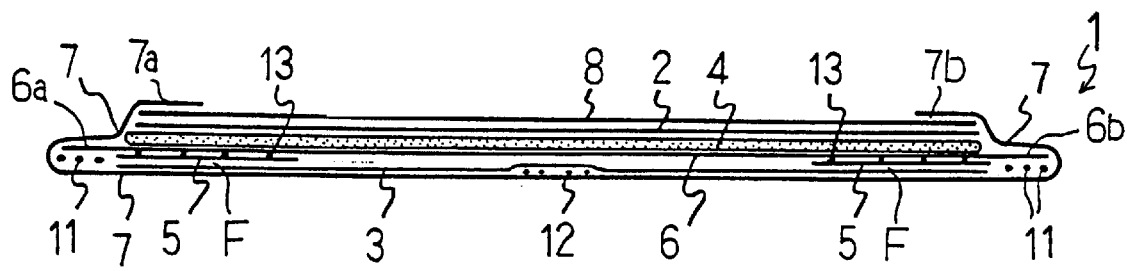
FIG. 3 is a schematic sectional view taken on line III—III of FIG. 2.
Figure 4:
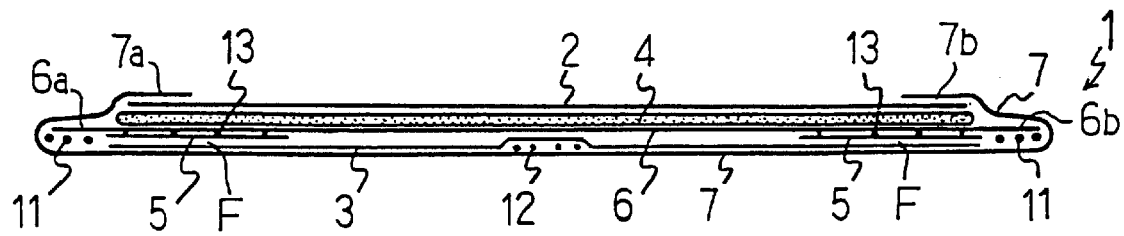
FIG. 4 is a schematic sectional view taken on line IV—IV of FIG. 2.
Figure 5:
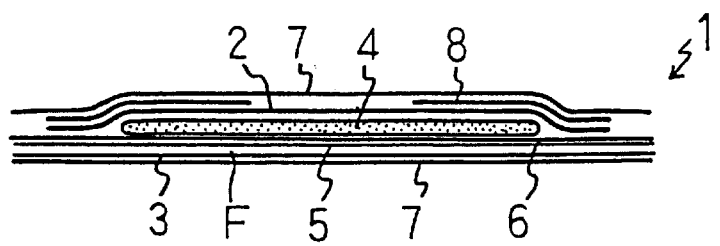
FIG. 5 is a schematic sectional view taken on line V—V of FIG. 2.
Figure 6:
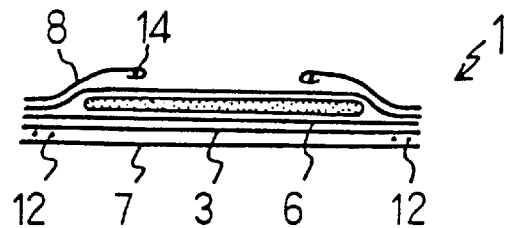
FIG. 6 is a schematic sectional view taken on line VI—VI of FIG. 2.
Figure 7:
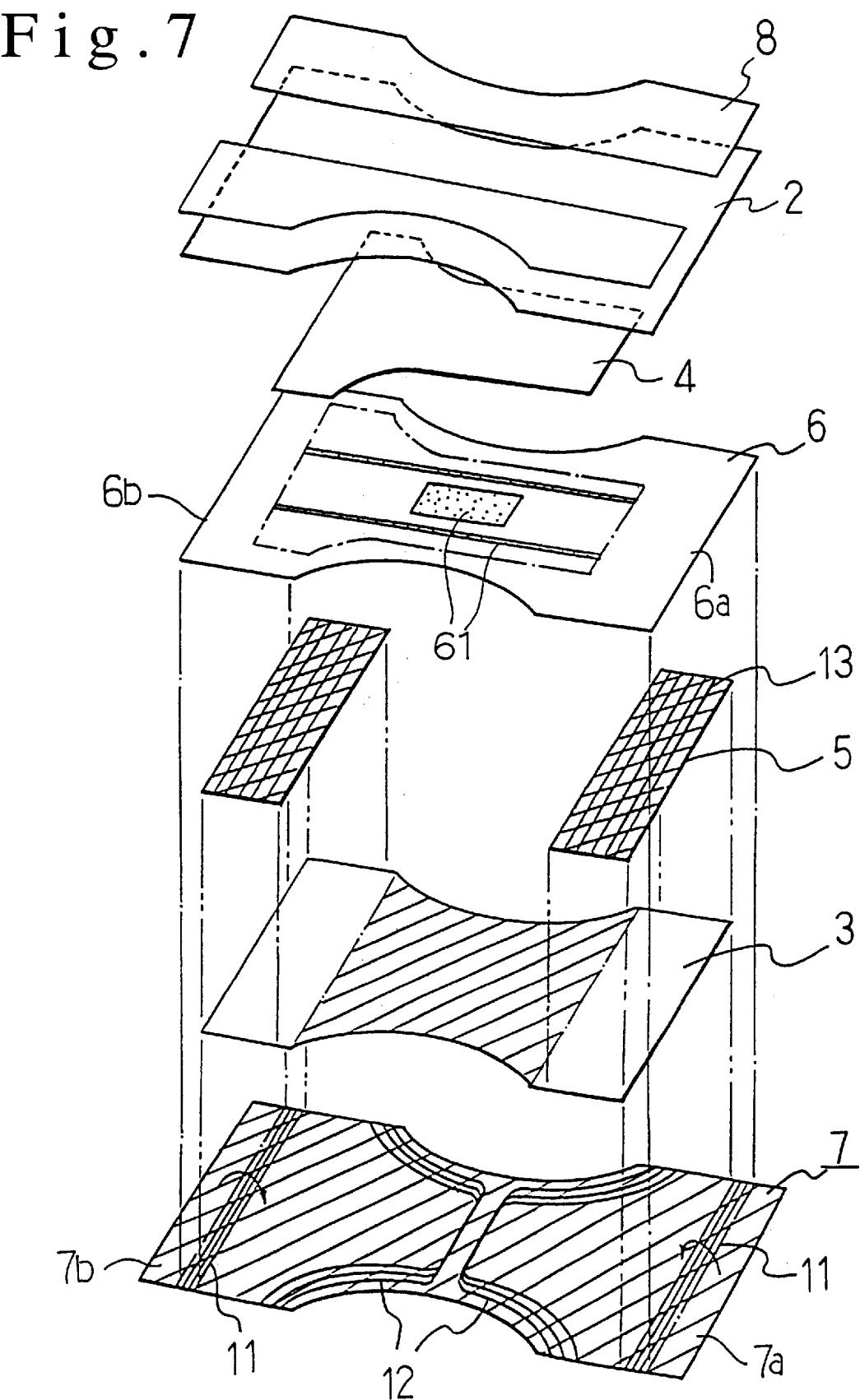
FIG. 7 is an exploded perspective view of the disposable diaper of FIG. 2.

FIG. 1 is a front view showing a disposable diaper as the first preferred embodiment of a disposable wearing article according to the present invention. FIG. 2 is a developed view of the disposable diaper of the embodiment shown in FIG. 1, FIG. 3 is a sectional view taken on line III—III of FIG. 2, FIG. 4 is a sectional view taken on line IV—IV of FIG. 2, FIG. 5 is a sectional view taken on line V—V of FIG. 2, and FIG. 6 is a sectional view taken on line VI—VI of FIG. 2. FIG. 7 is an exploded perspective view of the disposable diaper shown in FIG. 2.

A disposable diaper 1 according to the first embodiment shown in FIG. 1 and FIG. 2 includes a liquid-permeable topsheet 2, an outermost layer sheet 7 located on an outer surface of the disposable diaper 1, and a liquid retentive absorbent member 4. A waist-surrounding elastic member 13 being arranged at a waist-surrounding portion E.

The waist-surrounding elastic member 13 is fixed in its expanded state to members other than the outermost layer sheet 7 to thereby form gathers, a non-bonding area F is provided between the waist-surrounding elastic member 13 and the outermost layer sheet 7, and no gathers are formed on an outer surface of the waist-surrounding portion E. The expression "fix to members other than the outermost layer sheet" used herein means the state that the member 13 is fixed to members including the topsheet, the absorbent member, etc.other than the outermost layer sheet, but it is not fixed to the outermost layer sheet.

A disposable diaper according to this embodiment will be described in more detail. It has a liquid-impermeable backsheet 3. The absorbent member 4 is interposed between the topsheet 2 and the backsheet 3. Sheets for fixing elastic member (hereinafter referred to as "elastic member fixing sheets") 5 are disposed on an inner surface side of the backsheet 3. An inner layer sheet 6, on which the absorbent member 4 is placed, is disposed on the inner surface side of the backsheet 3. The waist-surrounding elastic member 13 is fixedly held between the inner layer sheet 6 as a member other than the outermost layer sheet 7 and the elastic member fixing sheets 5. The backsheet 3 is not bonded to the elastic member fixing sheets 5, which are the sheets located immediate to the inner surface of the backsheet 3, at the area where the waist-surrounding elastic member 13 is located. That is, the backsheet 3 is not bonded at its inner surface to the elastic member fixing sheets 5 but it is bonded to the inner sheet 6, at the area where the elastic member fixing sheets 5 are not bonded. The backsheet 3 is bonded generally over the entire outer surface thereof to the outermost layer sheet 7.

The elastic member fixing sheets 5 are disposed between the backsheet 3 and the inner layer sheet 6.

In the disposable diaper 1 of this embodiment, the waist portion elastic member 11 is disposed at the waist opening portion C, a leg portion elastic member 12 is disposed at the leg portion D, and the waist-surrounding elastic member 13 is disposed at the waist-surrounding portion E located below the waist opening portion C. That is, in this embodiment, the waist-surrounding portion E is an area located below the waist opening portion both on a stomach side portion and a back side portion as shown in FIG. 2.

As shown in FIGS. 1 and 2, the disposable diaper 1 according to this embodiment is a shorts type disposable diaper comprising left and right side edge portions Bi, B2 of a stomach side portion B, and a left and right edge portions A1, A2 ofthe back side portion A fixedly joined, respectively.

As shown in FIGS. 2 to 7, the backsheet 3 is not bonded at its inner surface to the elastic member fixing sheets 5 but it is bonded to the inner layer sheet 6 at a portion where the elastic member fixing sheets 5 are not bonded. Also, the backsheet 3 is bonded at its entire surface on its outer surface side to the outer layer sheet 7.

That is, the disposable diaper 1 according to the present invention is, as shown in FIGS. 2 to 7, constructed as follows.

In the disposable diaper 1 of this embodiment, the backsheet 3 is curvedly formed into a concave hourglass configuration at its under-crotch area. The absorbent member 4 is of a T-shaped configuration and arranged such that it is located generally at the center of the backsheet 3. The topsheet 2 is smaller than the backsheet 3. The topsheet 2 is curvedly formed into a concave hourglass configuration at its under-crotch area. The topsheet 2 is arranged such that it covers the absorbent member 4.

The outermost layer sheet 7 disposed on the outer surface side (outer surface side of the diaper) of the backsheet 3 is generally the same in configuration as the backsheet 3 but longer than the backsheet 3 at its front and back end portions 7a, 7b.

The inner layer sheet 6 disposed on the inner surface side (the surface side located on the absorbent member 4 side) of the backsheet 3 is also generally the same in configuration as the backsheet 3. The inner layer sheet 6 is longer at its front and rear end portions 6a, 6b than the backsheet 3 but shorter than the outermost layer sheet 7.

The rectangular elastic member fixing sheets 5 are disposed at a portion (both the stomach side portion B and the back side portion A) located at the waist surrounding portion E of the diaper.

The disposable diaper 1 is provided on its longitudinal left and right sides with nonwoven fabrics to thereby form cubic guards 8 respectively. A cubic guard expansible member 14 is disposed at a free end 81 of each cubic guard 8, to thereby form a cubic gather.

The outermost layer sheet 7 is folded back at its front and rear end portions 7a, 7b at front and rear end edges of the diaper and fixedly secured thereto in such a manner as to cover the front and rear both end edge portions of the absorbent member, the topsheet 2 and the cubic guard 8.

The waist portion elastic member 11 and the leg portion elastic members 12 for fitting, when in wear, the waist opening portion C and the leg portions D to the wearer are disposed, respectively, on the waist opening portion C and the leg portions D at a peripheral edge portion of the absorbent member 4. The waist portion elastic member 11 consists of a plurality of linearly arranged elastic straps (three straps in this embodiment), and the leg portion elastic members 12 each consist of a plurality of U-shaped elastic straps (two straps in this embodiment) provided on both the stomach side portion B and the back side portion A. The waist portion elastic member 11 is fixedly held between the outermost layer sheet 7 and the inner layer sheet 6, while the leg elastic members 12 are fixedly held between the outermost layer sheet 7 and the backsheet 3.

The waist-surrounding elastic member 13 is fixedly held between the elastic member fixing sheets 5 and the inner layer sheet 6.

The absorbent member 4 is bonded to the inner layer sheet 6 through an adhesive agent 61 linearly and rectangularly applied thereto.

The elastic member fixing sheets 5, whose generally entire inner surface (that surface located on the absorbent member 4 side) is applied with an adhesive agent (the area indicated by phantom lines of FIG. 7), is bonded to the inner layer sheet 6. The area shown by phantom lines in exploded perspective view indicates that an adhesive agent is applied thereto. The area shown by dashed phantom lines indicates that an adhesive agent is applied to the back side area of the side shown in the views. The same explanation is applicable to each embodiment mentioned below. The backsheet 3, which is applied with an adhesive agent (the area indicated by phantom lines of FIG. 7) at an area not contacting the elastic member fixing sheets 5, is bonded to the inner layer sheet 6. That is, The elastic member fixing sheets 5 and the backsheet 3 are not bonded with each other. The outermost layer sheet 7, whose generally entire surface is applied with an adhesive agent (the area indicated by phantom lines of FIG. 7), is bonded to the entire surface of the backsheet 3 and is also bonded at its front and rear end edge portions 7a, 7b to the both front and rear end edge portions 6a, 6b of the inner layer sheet 6. Also, the outermost layer sheet 7 is fixed at its folded back portion to the front and rear end edge portions of the topsheet 2 and the cubic guard 8.

Since the disposable diaper 1 according to this embodiment is fixedly held at its waist-surrounding elastic member 13 between the elastic member fixing sheets 5 and the inner layer sheet 6 and not fixed, directly or indirectly, to the backsheet 3 and therefore, to the outermost layer sheet 7, the non-bonding area F is provided between the waist-surrounding elastic member 13 and the outermost layer sheet, and no gathers are formed on the waist-surrounding portion E in the outer surface of the diaper by the waist-surrounding elastic member 13. Accordingly, by the function of the waist-surrounding elastic member 13, fittability of the waist-surrounding portion E, and therefore, fittability of the diaper as a whole can be enhanced when in wear, without deteriorating the outer appearance of the diaper.

According to the disposable diaper of this embodiment, the follow effects can further be exhibited.

It has a cloth-like neat outer appearance and is favorable in fitness.

Wearing of the diaper is not conspicuous even on tight trousers/skirt/pants.

When the diaper and trousers are pulled up, they can be smoothly pulled up without being caught.

In case a pattern and a print are applied, the printed pattern is prevented from deterioration in outward appearance due to shrinkage.

In case a tape to be discarded is employed, bonding can be made easily in processing and productivity is enhanced.

A tape to be discarded is prevented from being shrunk or peeled off at its corners because it is collected by gathers. Also, when discarding, the bonding surface of the tape is flat and smooth and therefore, the discarding operation is easy.

If a sheet having a high consealabilty (water-proof film in particular) is used as a sheet located outwardly of the waist-surrounding elastic member, a more favorable effect can be obtained.

Material for forming the component members constituting the disposable diaper 1 will now be described.

The topsheet 2 is preferably a liquid-permeable sheet for enabling waste material to permeate to the absorbent member 4 and preferably has a feel something like an undergarment. Example of such liquid-permeable sheet are preferably woven fabrics, nonwoven fabrics, perforated films and the like. The permeation leakage of waste materials such as urine and the like from the edge portion of the topsheet 2 can be prevented by applying a water repellent treatment to the peripheral edge portion of the topsheet 2 by a method for applying a hydrophobic compound such as siliconbased oil solution, paraffin wax and the like to the peripheral edge portion of the topsheet 2 or by a method for applying a hydrophilic compound such as alkyl phosphoric ester to the entirety in advance and then cleaning the peripheral edge with hot water.

The backsheet 3 is preferably a liquid-impermeable and moisture-permeable sheet formed of a thermoplastic resin and filler added thereto and stretched or a laminated sheet composed of a fibers aggregation and the film sheet.

The absorbent member 4 is preferably composed of a fluff pulp as a chief component material and a high molecular water absorbent polymer as a secondary material. The high molecular water absorbent polymer may be located in an upper layer, an intermediate layer or a lower layer of the absorbent member 4, or it may be mixed with pulp. The high molecular absorbent polymer preferably has a liquid retentive ability capable of absorbing and retaining liquid more than twenty times the dead weight thereof and is in a grain shape readily gelled. Examples of such high molecular water absorbent polymer are preferably starch-acrylic (salt) graft copolymer, a saponified material of starch-acrylonitrile copolymer, bridged material of sodium carboxymethyl cellulose, acrylic (salt) polymer and the like.

The waist portion elastic member 11, the leg portion elastic members 12, the waist-surrounding elastic member 13, and the cubic elastic member 14 are preferably a thread rubber, a flat rubber, a film type rubber or polyurethane, or an elastic film, a thread rubber, a flat rubber, a foamed member of ethylene-$\beta$-olefin copolymer manufactured by using a metallocene catalyst, and particularly preferably 40 to 150 g in stress when stretched 50%.

As the nonwoven fabric forming the cubic guard 8, those which are normally used in diapers can be used without any particular limitation.

Also, as the outermost layer sheet 7, the inner layer sheet 6 and elastic member fixing sheet 5, nonwoven fabrics, plastic films such as polyethylene, urethane and the like, and a lamination thereof, which are manufactured by various kinds of methods and usually used as sanitary material can be used.

The disposable diaper according to this embodiment can be used in the same manner as the normal shorts type disposable diaper, and it can be manufactured in the following manner.

That is, as shown in FIG. 7, the absorbent member 4, the topsheet 2, and the cubic guard 8 are placed in this order on the inner surface of the inner layer sheet 6, and the elastic member fixing sheets 5 with the waist-surrounding elastic member 13 fixed thereto are provided on the front and rear both end portions 6a, 6b side of the outer surface side (backsheet 3 side) of the inner sheet 6, and then the backsheet 3 whose area contacting the elastic member fixing sheets 5 is not applied with an adhesive agent and whose area directly contacting the inner layer sheet 6 is applied with an adhesive agent is bonded thereto. Then, the outermost layer sheet 7 applied with an adhesive agent over the entire surface thereof and having the waist portion elastic member 11 and the leg portion elastic members 12 arranged in predetermined locations thereof is bonded to the backsheet 3 and the inner layer sheet 6. Thereafter, the front and rear both end edge portions 7a, 7b of the outermost layer sheet 7 are folded back in directions as indicated by arrows to fix the topsheet 2 and the cubic guard 8. By doing so, the disposable diaper according to this embodiment can be obtained.

Although the disposable diaper of the present invention has been hereinbefore described in the form of one preferred embodiment, the disposable diaper of the present invention is not limited to the above embodiment but many changes can be made.

For example, in the above-mentioned embodiment, the waist portion elastic member 11 and the leg portion elastic members 12 may be fixed by the backsheet 3, which is used as the outermost layer sheet, and the inner layer sheet 6 without providing the outermost layer sheet 7; the waistsurrounding elastic member 13 may be fixed by the absorbent member 4 and the topsheet 2, and the elastic member fixing sheets 5 without providing the inner layer sheet 6; and the waist-surrounding elastic member 13 may be fixed by the absorbent member 4 and the topsheet 2, and the elastic member fixing sheets 5 by using the backsheet 3 as the outermost layer sheet without providing the inner layer sheet 6 and the outermost layer sheet 7.

While the explanation of the waist-surrounding elastic member in the above-mentioned embodiments was made by exemplifying the case where it is provided over the entire circumferential area around the waist-surrounding portion, the waist-surrounding elastic member may be provided not over the entire circumferential area but on the part of the waist-surrounding portion.

The second through fourth embodiments will now be described with reference to FIGS. 8 to 10.

Figure 8:
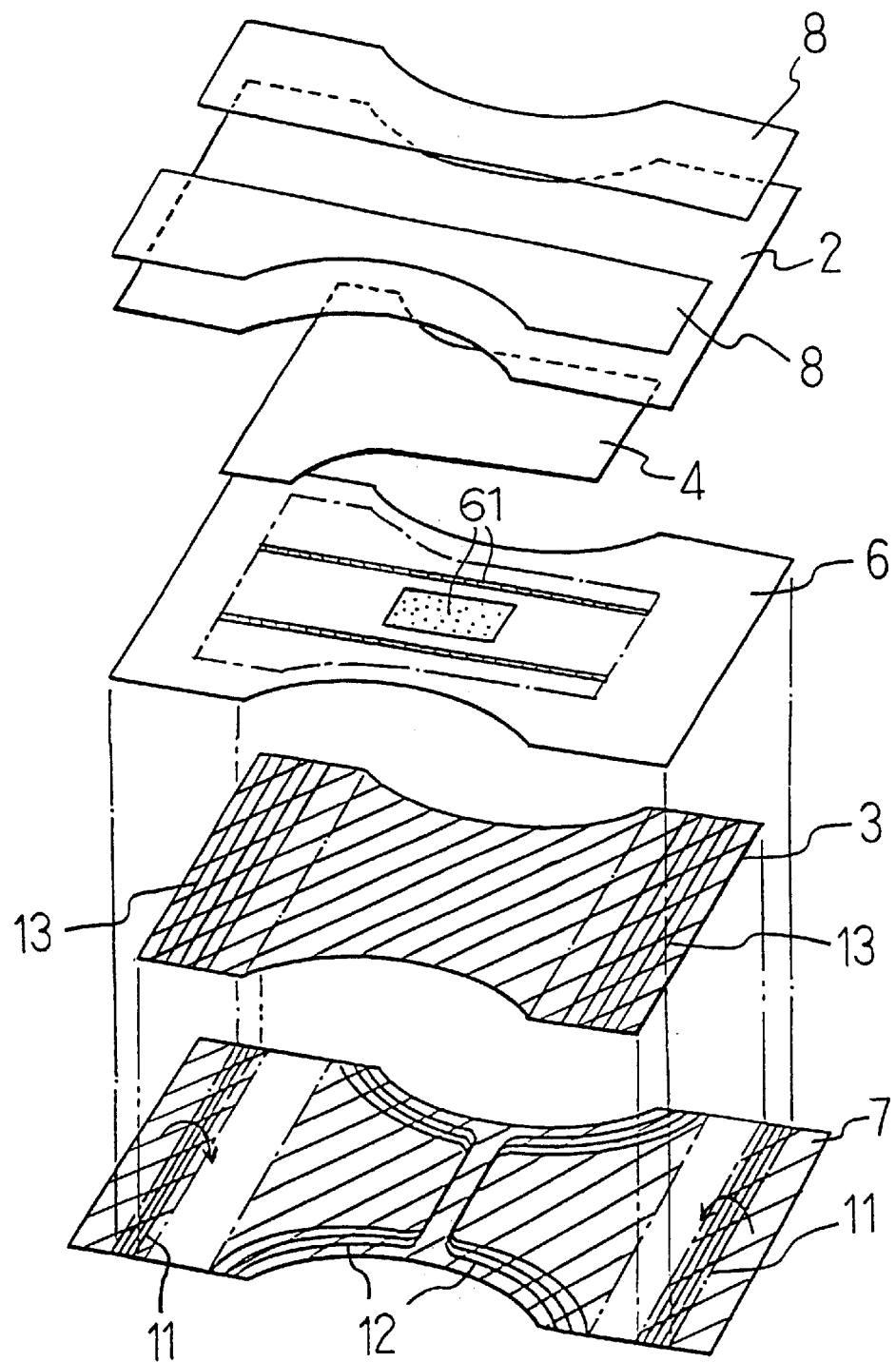
FIG. 8 is an exploded perspective view of a disposable diaper showing the second embodiment.
Figure 9:
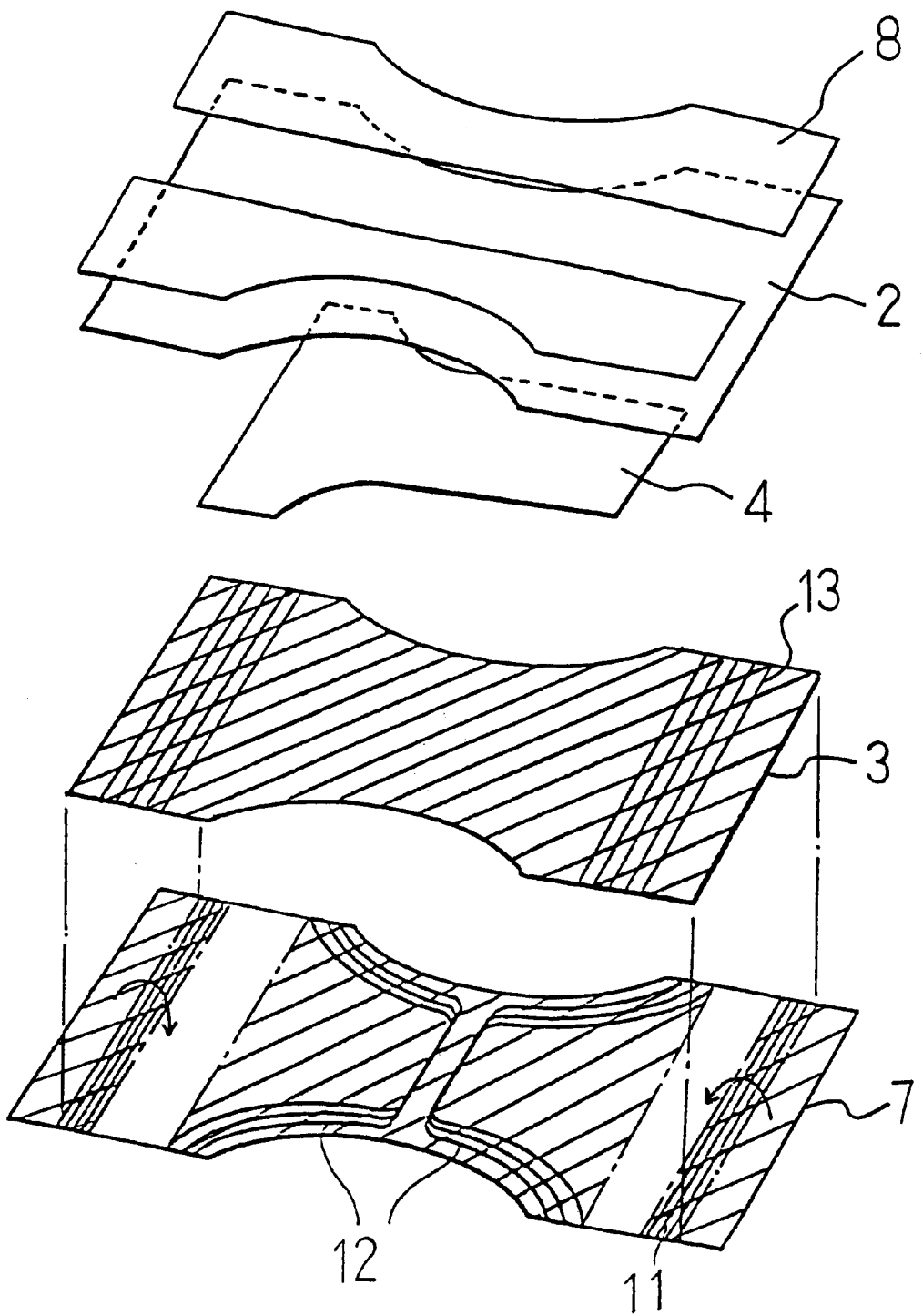
FIG. 9 is an exploded perspective view of a disposable diaper showing the third embodiment.
Figure 10:
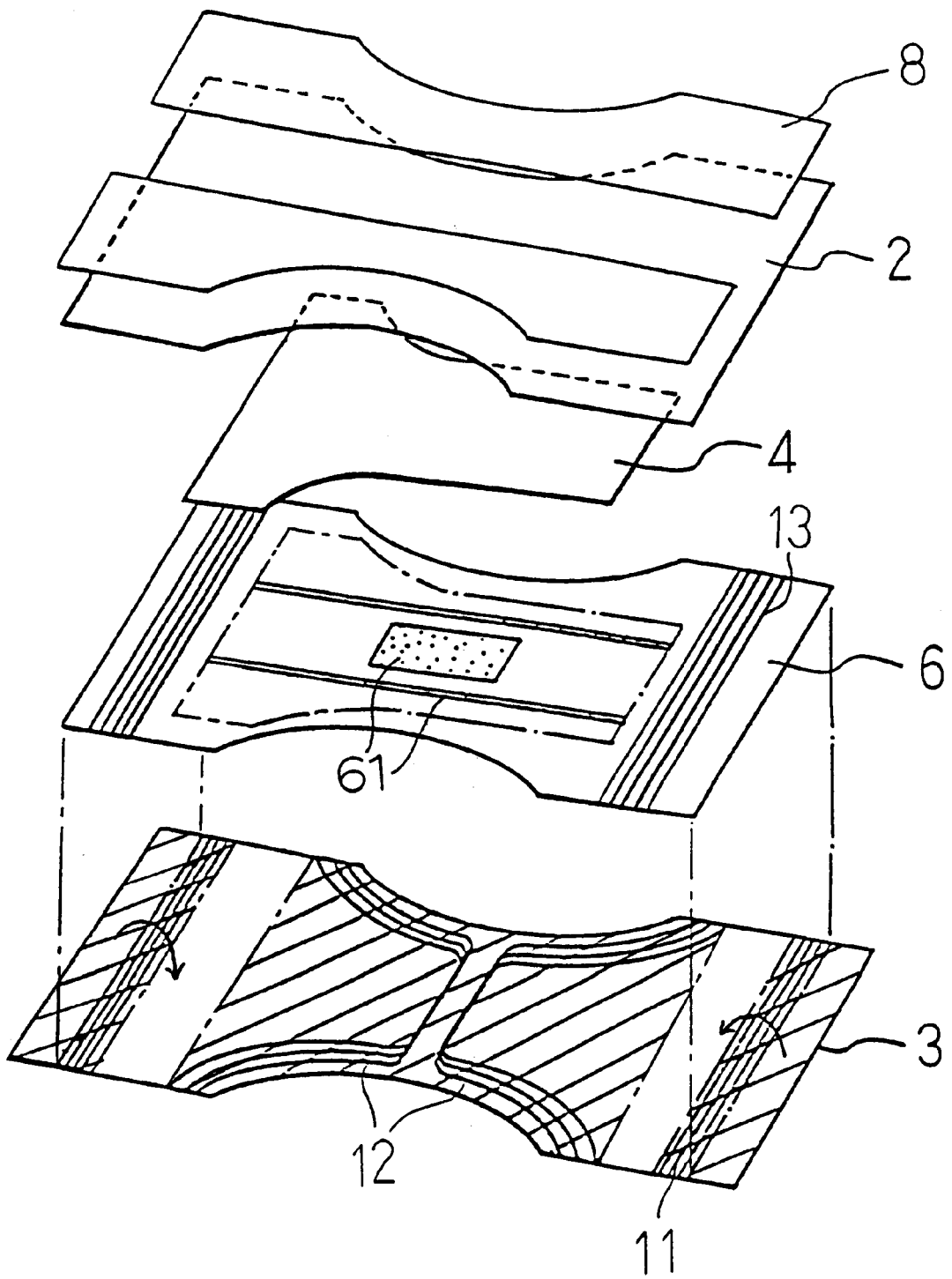
FIG. 10 is an exploded perspective view of a disposable diaper showing the fourth embodiment.

Here, FIG. 8 is an exploded perspective view of a diaper showing the second embodiment, FIG. 9 is an exploded perspective view of a diaper showing the third embodiment, and FIG. 10 is an exploded perspective view of a diaper showing the fourth embodiment.

In the description of the embodiments to follow, different points from the embodiment according to the first embodiment will be particularly described in detail. With respect to those points not particularly described in detail, the description made in the description on the first embodiment is applicable, where appropriate.

A disposable diaper 1 according to the second embodiment shown in FIG. 8 includes a liquid-impermeable backsheet 3, an absorbent member 4 being interposed the topsheet 2 and the backsheet 3, an inner layer sheet 6, on which the absorbent member 4 is placed, being arranged on an inner surface of the backsheet 3, and a waist-surrounding elastic member 13 being arranged on an inner surface side of the backsheet 3.

The waist-surrounding elastic member 13 is disposed on an inner surface side (topsheet 2 side) of the backsheet 3, and no gathers are formed on an outer surface of the waist-surrounding portion E.

Specifically, the backsheet 3 is bonded over its entire surface to the inner layer sheet 6.

The waist-surrounding elastic members 13 is provided on the waist's surrounding portion E of its back side portion A and stomach side portion B. The waist-surrounding elastic member 13 is fixedly held between the backsheet 3 and the inner layer sheet 6 at a location between the backsheet 3 and the topsheet 2.

The waist-surrounding portion E on which the waist-surrounding elastic members 13 of the backsheet 3 are disposed, is not bonded to the outermost layer sheet 7 (the portion not indicated by phantom lines of FIG. 8). In doing so, a non-bonding area F is provided between the waist-surrounding elastic member 13 and the outermost layer sheet, so that no gathers are formed on the waist-surrounding portion E of the outer surface of the diaper.

The disposable diaper according to the third embodiment shown in FIG. 9 includes a liquid-impermeable backsheet 3, the absorbent member 4 being interposed between the topsheet 2 and the backsheet 3, and no inner layer sheet 6 being provided. A waist-surrounding elastic member 13 is arranged on an inner surface side (topsheet 2 side) of the backsheet 3, and no gathers are formed on a waist-surrounding portion E in an outer surface of the diaper.

Specifically, in the disposable diaper 1 according to the third embodiment shown in FIG. 9, the waist-surrounding elastic member 13 is fixedly held between the backsheet 3 and the topsheet 2. The backsheet 3 and the outermost layer sheet 7 are bonded together through an adhesive agent (the portion indicated by the phantom lines of FIG. 9), only excepting the waist-surrounding portion E where the waist-surrounding elastic member 13 is disposed. Accordingly the backsheet 3 and the outermost layer sheet 7 are not bonded together at the area (the waist-surrounding portion E) where the waist-surrounding elastic members 13 are disposed. In doing so, a nonbonding area F is provided between the waist-surrounding elastic member 13 and the outermost layer sheet 7 so that no gathers are formed on the outer surface of the diaper.

A disposable diaper 1 according to the fourth embodiment shown in FIG. 10 includes a liquid-impermeable backsheet 3, an absorbent member 4 being interposed the topsheet 2 and the backsheet 3, an inner layer sheet 6, on which the absorbent member 4 is placed, being arranged on an inner surface of the backsheet 3, and a waist-surrounding elastic member 13 being arranged on an inner surface side of the backsheet 3.

No outermost layer sheet 7 is provided, and the backsheet 3 is used as the outermost sheet. The waist-surrounding elastic member 13 is disposed on an inner surface side (topsheet 2 side) of the backsheet 3, but no gathers are formed on the waist-surrounding portion E in an outer surface of the diaper. In this way, the outermost layer sheet may be replaced with the backsheet without using any special member.

Specifically, in the disposable diaper according to the fourth embodiment shown in FIG. 10, the waist-surrounding elastic member 13 is fixedly held between the inner layer sheet 6 and the topsheet 2. The inner layer sheet 6 and the backsheet 3 are bonded together through an adhesive agent (the portion indicated by the phantom lines of FIG. 10), only excepting the waist-surrounding portion E where the waist-surrounding elastic member 13 is disposed. Accordingly the backsheet 3 and the inner layer sheet 6 are not bonded together at the area (the waist-surrounding portion E) where the waist-surrounding elastic members 13 are disposed. In doing so, a nonbonding area F is provided between the waist-surrounding elastic member 13 and the backsheet 3 as the outermost layer sheet, so that no gathers are formed on the outer surface of the diaper.

In the second to fourth embodiments, the disposable diaper can also be manufactured and used almost in the same manner as in the first embodiment. And the same effect as in the first embodiment can be exhibited.

The fifth to ninth embodiments of the present invention will now be described with reference to FIGS. 11 through 21.

Figure 11:
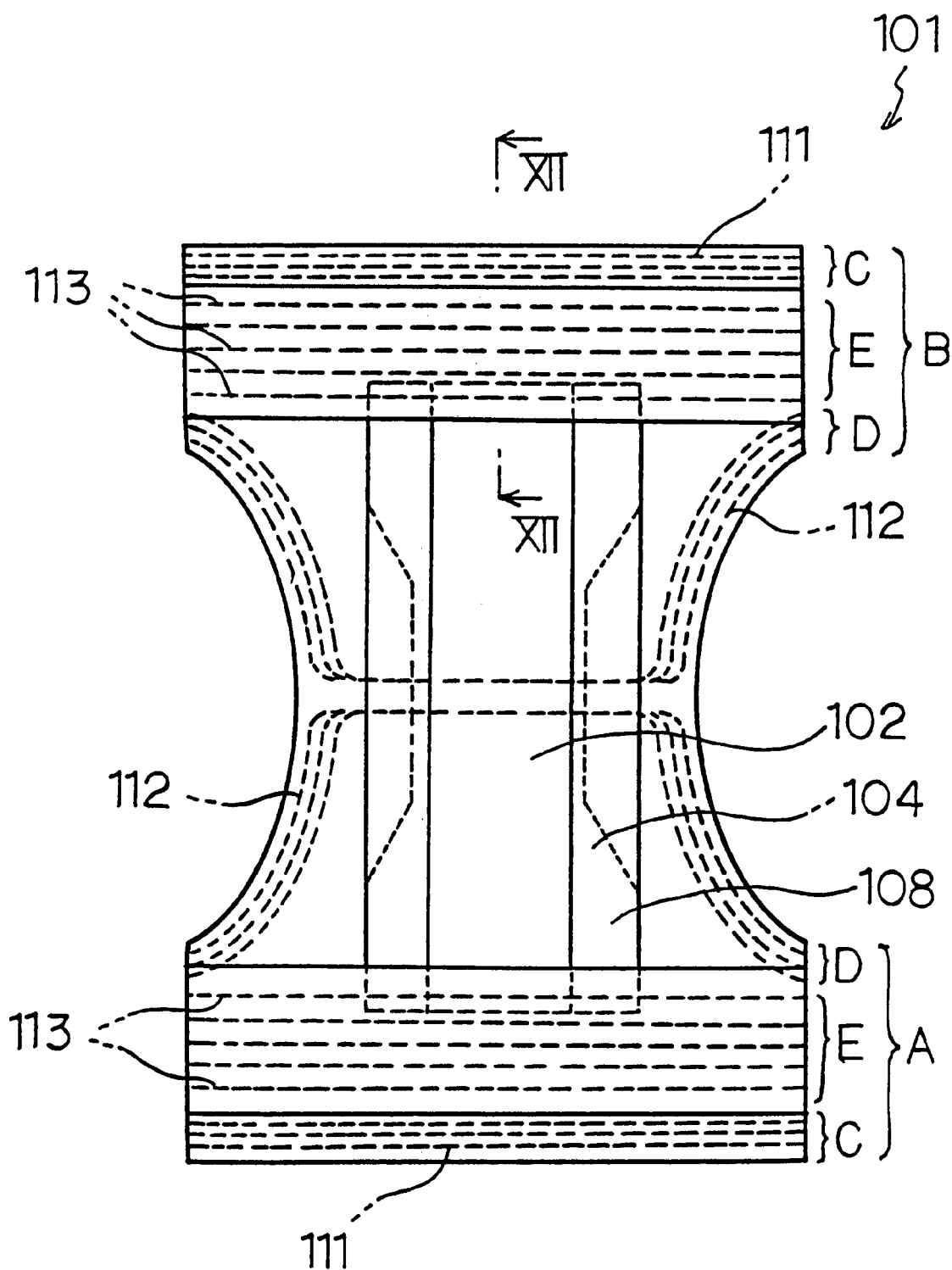
FIG. 11 is a developed plan view showing the fifth embodiment of the present invention.
Figure 12:
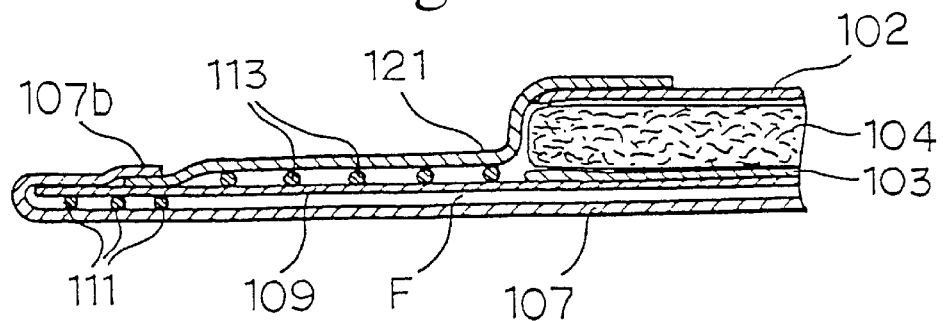
FIG. 12 is a schematic sectional view taken on line XII—XII of FIG. 11.
Figure 13:
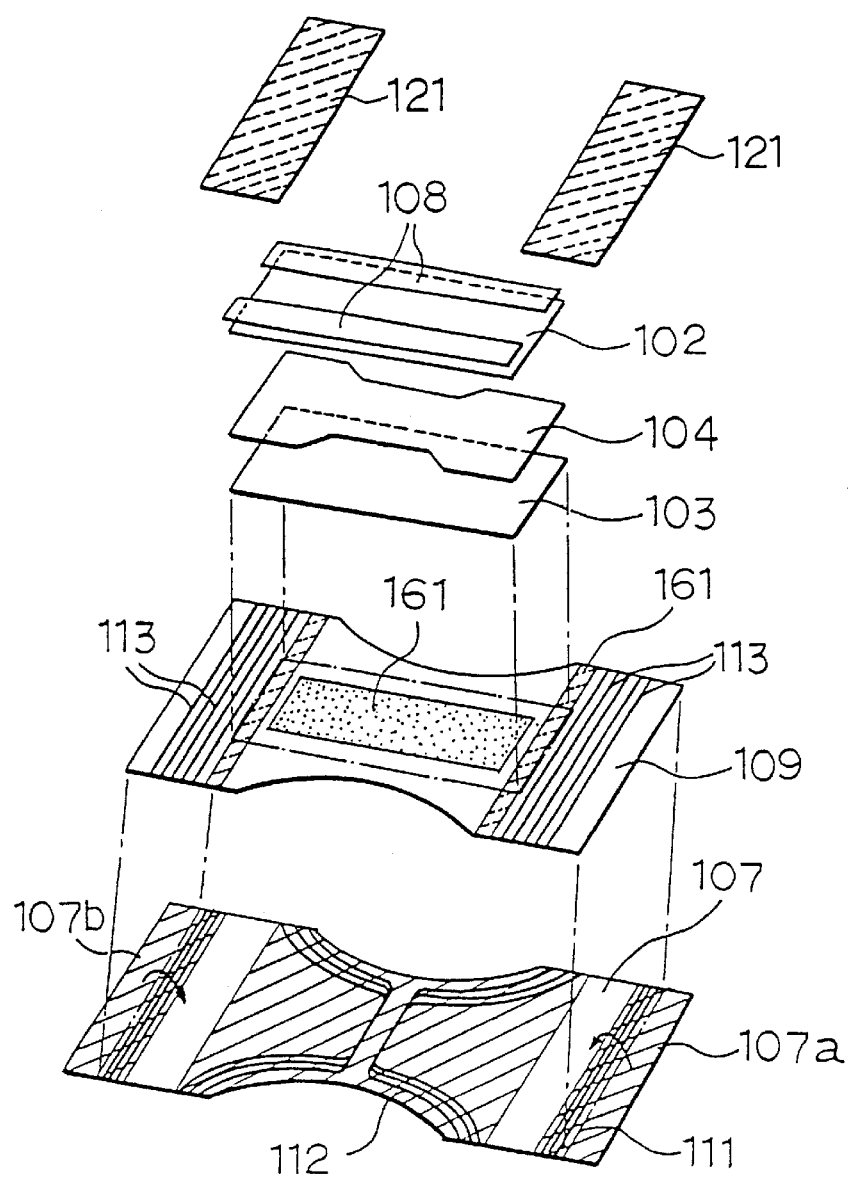
FIG. 13 is an exploded perspective view of the disposable diaper of FIG. 11.
Figure 14:
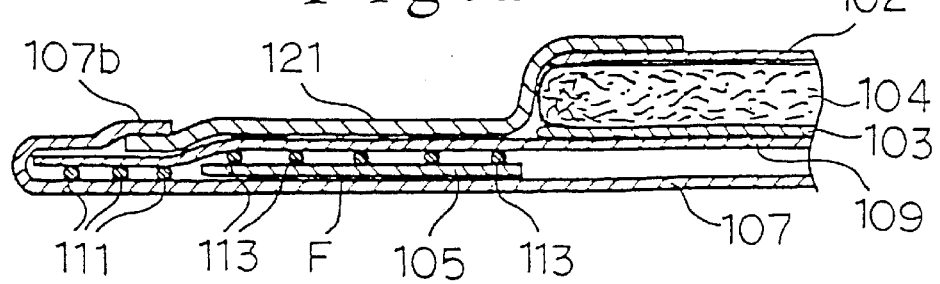
FIG. 14 is a schematic longitudinal sectional view (corresponding to FIG. 12) showing the sixth embodiment of the present invention.
Figure 15:
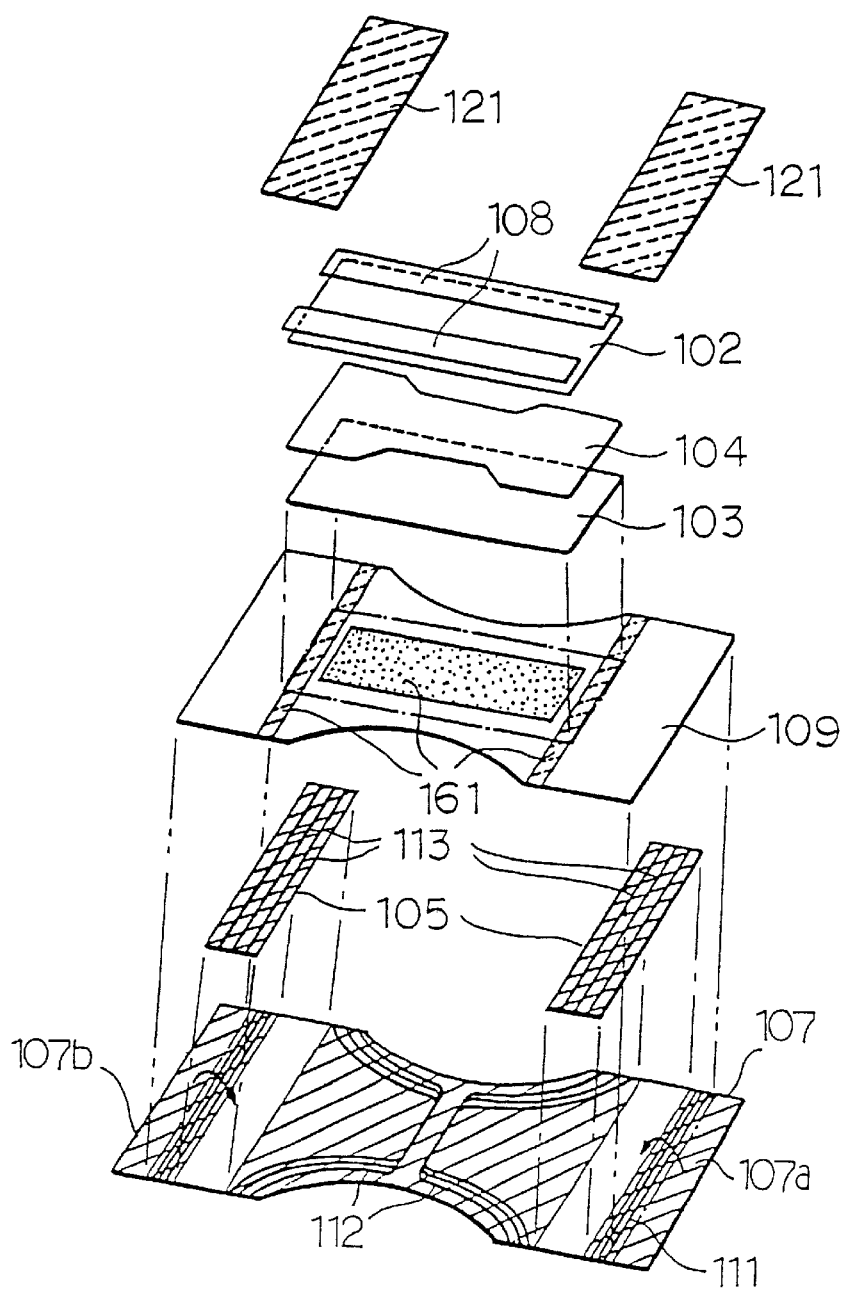
FIG. 15 is an exploded perspective view (corresponding to FIG. 13) of the disposable diaper of FIG. 14.
Figure 18:
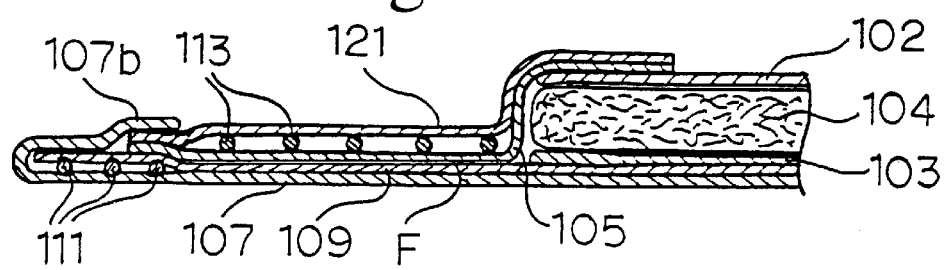
FIG. 18 is a schematic longitudinal sectional view (corresponding to FIG. 12) showing the eighth embodiment of the present invention.
Figure 19:
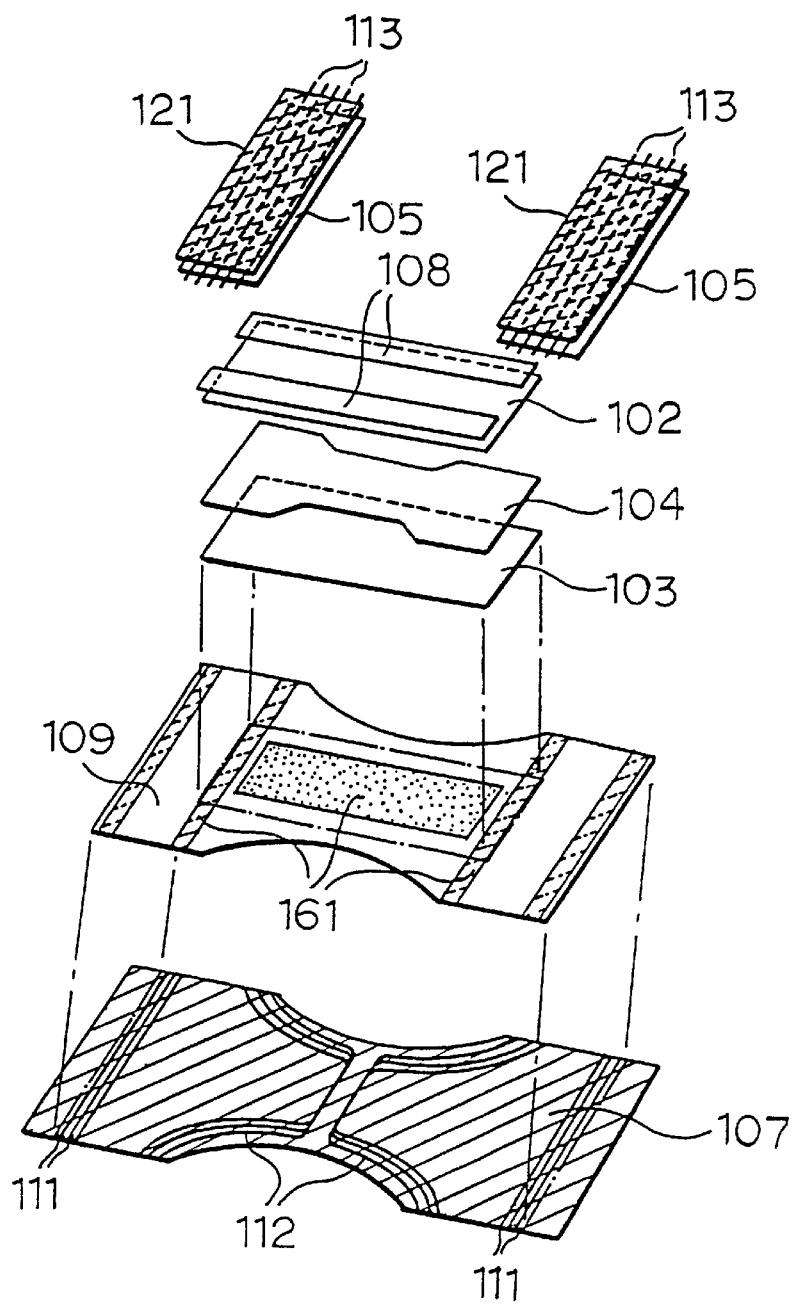
FIG. 19 is an exploded perspective view (corresponding to FIG. 13) of the disposable diaper of FIG. 18.

Here, FIG. 11 is a developed plan view showing the fifth embodiment of the present invention. FIG. 12 is a sectional view taken on line XII—XII of FIG. 11, and FIG. 13 is an exploded perspective view of the disposable diaper of FIG. 11. FIG. 14 is a longitudinal sectional view (corresponding to FIG. 12) of the sixth embodiment of the present invention, and FIG. 15 is an exploded perspective view (corresponding to FIG. 13) of the disposable diaper of FIG. 14. FIG. 16 is a longitudinal sectional view (corresponding to FIG. 12) of the seventh embodiment of the present invention, and FIG. 17 is an exploded perspective view (corresponding to FIG. 13) of the disposable diaper of FIG. 16. FIG. 18 is a longitudinal sectional view (corresponding to FIG. 12) of the eighth embodiment of the present invention, and FIG. 19 is an exploded perspective view (corresponding to FIG. 13)

of the disposable diaper of FIG. 18. FIG. 20 is a longitudinal sectional view (corresponding to FIG. 12) of the ninth embodiment of the present invention, and FIG. 21 is an exploded perspective view (corresponding to FIG. 13) of the disposable diaper of FIG. 20.

The fifth embodiment will be described first. In the description of the fifth to ninth embodiments which will be described hereinafter, the same members as those in the above-mentioned first embodiment are each assigned with a number between one and two hundreds and the same portions are not described in particular. Those portions not described in particular, the description made with reference to the first embodiment is applied, where appropriate.

A disposable diaper 101 according to the fifth embodiment shown in FIGS. 11 to 13 includes a liquid impermeable backsheet 103, an absorbent member 104 being interposed between the topsheet 102 and the backsheet 103, an outer layer sheet 109 being disposed between the back sheet 103 and an outermost layer sheet 107, and a waist-surrounding elastic member 113 being fixed directly to an outer layer sheet 109.

More specifically, as shown in FIGS. 11 and 13, the backsheet 103 and the topsheet 102 has a rectangular configuration, and the absorbent member 104 is curvedly formed into a concave hourglass configuration at its under-crotch area. Cubic guards 108 are each arranged on both left and right side edge portions above the topsheet 102.

The outermost layer sheet 107 and the outer layer sheet 109 are also generally the same in configuration, which is curvedly formed into a concave hourglass configuration at its under-crotch area. However, both front and rear end portions 107*a*, 107*b* of the outermost layer sheet 107 are longer than the outer layer sheet 109.

Rectangular inner sheets 121 are disposed on an outer surface side of the outer layer sheet 109 in such a manner as to cover end edges of the topsheet.

Both front and rear end portions 107*a*, 107*b* of the outermost layer sheet 107 are folded back at both front and rear end edges of the diaper and firmly secured in such a manner as to cover end edge portions of the outer layer sheet 109 and the inner sheet 121.

The waist portion elastic member 111 and the leg portion elastic member 112 are fixedly held between the outermost layer sheet 107 and the outer layer sheet 109.

The waist-surrounding elastic member 113 is firmly secured directly to an outer surface side (skin-contacting surface side) of the outer layer sheet 109 and fixedly held between the outer layer sheet 109 and the inner sheet 121.

The backsheet 103 is bonded to the outer layer sheet 109 through an adhesive agent 161 linearly and rectangularly applied to a generally central portion of the outer layer sheet 109.

An adhesive agent is applied to whole area (the area indicated by phantom lines of FIG. 13) of the outermost layer sheet 107 only excepting the waist-surrounding portion E, so that the outer layer sheet 109 and the outermost layer sheet 107 are not bonded together at the waist-surrounding portion E. The outer layer sheet 109 and the outermost layer sheet 107 are bonded together at the areas excepting the waistsurrounding portion E through an adhesive agent. By this, a non-bonding area F is provided between the waist-surrounding elastic member 113 and the outermost layer sheet 107, so that no gathers are formed on an outer surface of the disposable diaper.

As the material for forming the outer layer sheet 109 and the inner sheet 121, a nonwoven fabric, or plastic film such as polyethylene, urethane, or the like, and a lamination thereof, which are manufactured by various kinds of methods and usually used as sanitary material can be used.

In the fifth embodiment, the same effect as in the above-mentioned first embodiment can be exhibited. Also, a disposable diaper according to the fifth embodiment can be manufactured generally in the same manner as in the above-mentioned first embodiment.

In this embodiment, a part of the waist-surrounding elastic member may be disposed under the absorbent member.

The expression "directly or through other sheets" does not mean that the waist-surrounding elastic member is entirely bonded to the outer layer sheet, but means to include such a case that a part of the waist-surrounding elastic member is located above the absorbent member.

The sixth to ninth embodiments will be described hereinafter. In the description to follow, only those points which are different from the fifth embodiment are described in detail. Those points not described in particular are the same as the first and fifth embodiments and description thereof is applied, where appropriate.

In a disposable diaper according to the sixth embodiment shown in FIGS. 14 and 15, rectangular elastic member fixing sheets 105 are arranged between the outermost layer sheet 107 and the outer layer sheet 109 at the areas (both stomach side portion B side and back side portion A side) located on (i.e., corresponding to) the waist-surrounding portion E of the diaper.

The waist-surrounding elastic member 113 is fixedly held between the elastic member fixing sheets 105 and the outer layer 109.

The elastic member fixing sheets 105 are each applied over an entire inner surface (the surface on the absorbent member 4 side) thereof with an adhesive agent (the portion indicated by phantom lines of FIG. 15) and bonded to the outer layer sheet 109. The elastic member fixing sheets 105 and the outermost layer sheet 107 are not bonded together. Since the elastic member fixing sheets 105 and the outermost layer sheet 107 are not bonded together, a non-bonding area F is provided between the waist-surrounding elastic member 113 and the outermost layer sheet 107, so that no gathers are formed on an outer surface of the disposable diaper.

In a disposable diaper 101 according to the seventh embodiment shown in FIGS. 16 and 17, the waist-surrounding elastic member 113 is bonded to an inner sheet 121 and fixed held between the inner sheet 121 and the outer layer sheet 109.

The outermost layer sheet 107 is applied over its entire area (the area indicated by phantom lines of FIG. 13) only excepting the waist-surrounding portion E with an adhesive agent. The outer layer sheet 109 and the outermost layer sheet 107 are not bonded together at the waist-surrounding portion E, but they are bonded together at the area other than the waist-surrounding portion E through an adhesive agent. By this, a non-bonding area F is provided between the waist-surrounding elastic member 113 and the outermost layer sheet 107, so that no gathers are formed on an outer surface of the disposable diaper.

In a disposable diaper according to the eighth embodiment shown in FIGS. 18 and 19, elastic member fixing sheets 105 are arranged between an inner sheet 121 and an outer layer sheet 109.

A waist-surrounding elastic member 113 is fixedly held between the elastic member fixing sheets 105 and the inner sheet 121 and then placed on the outer layer sheet 109.

The elastic member fixing sheets 105 are each fixed only at their widthwise opposite end edge portions to the outer layer sheet 109 but they are not fixed at their waist-surrounding portion E thereto. An outermost layer sheet 107 and the outer layer sheet 109 are firmly secured together at their entire surfaces. Since the elastic member fixing sheets 105 and the outer layer sheet 109 are not bonded together at the waist-surrounding portion E, an non-bonding area F is provided between the waistsurrounding elastic member 113 and the outermost layer sheet 107 so that no gathers are formed on an outer surface of the disposable diaper.

In a disposable diaper according to the ninth embodiment shown in FIGS. 20 and 21, a waist-surrounding elastic member 113 is bonded to an outermost layer sheet 107 side of an outer layer sheet 109. However, in this embodiment, an adhesive agent is applied only to the outer layer sheet 109 side of the waist-surrounding elastic member 113 and the waist-surrounding elastic member 113 is bonded only to the outer layer sheet 109.

Owing to this arrangement, non-bonding area F is provided between the waist-surrounding elastic member 113 and the outermost layer sheet 107, so that no gathers are formed on an outer surface of the disposable diaper.

In the above-mentioned fifth to ninth embodiments, it is also acceptable that the outermost layer sheet 107 having extending longitudinal opposite end edge portions is used instead of using the inner sheet, and such extending portions are situated on the innermost surface.

Although the disposable diaper according to the above-mentioned fifth to ninth embodiments exhibits the same effect as the disposable diaper according to the first embodiment, it is particularly suited to be used as a wearing article for adults.

The tenth embodiment of the present invention will now be described in detail with reference to FIGS. 22 and 23.

Figure 22:
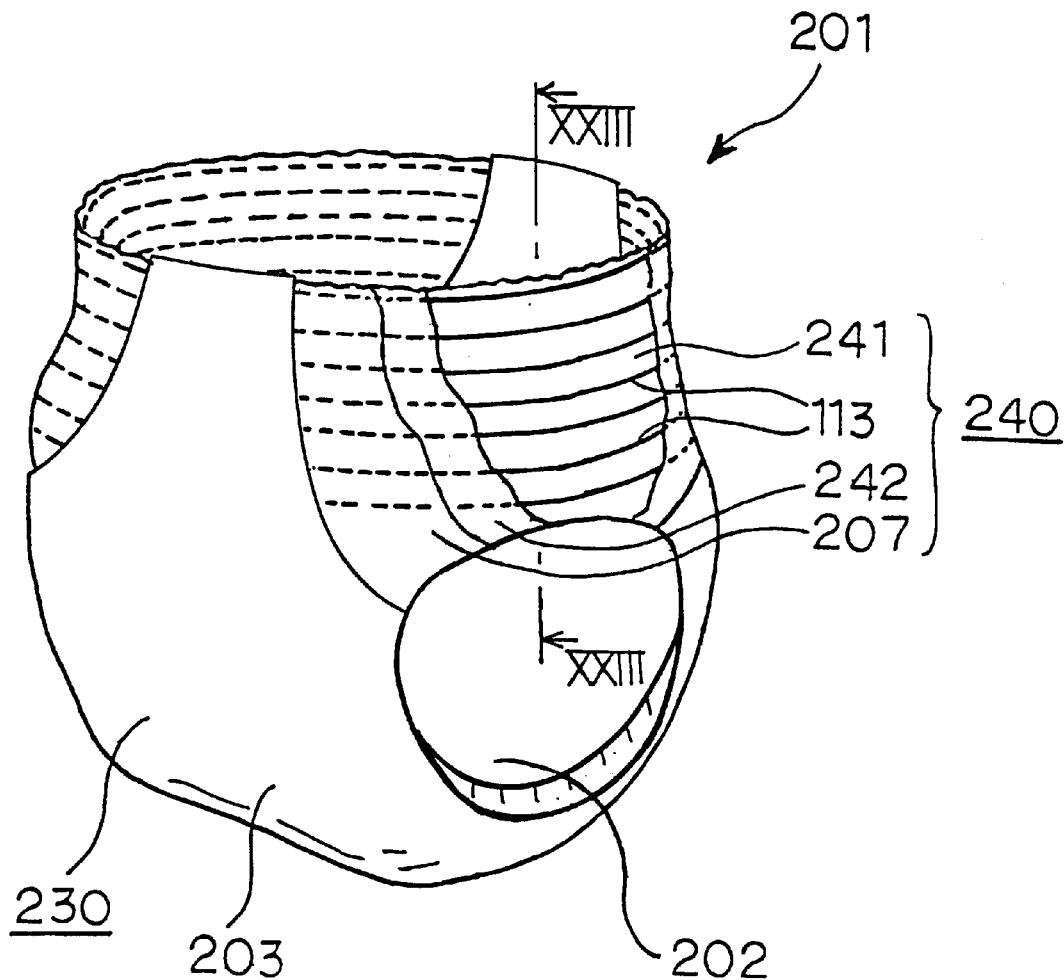
FIG. 22 is a perspective view showing the tenth embodiment of the present invention.
Figure 23:
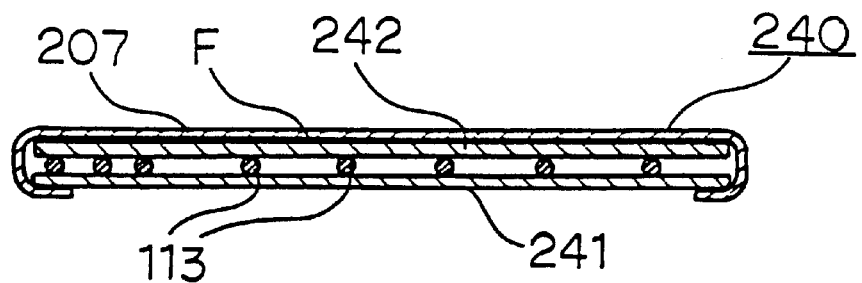
FIG. 23 is a schematic sectional view taken on line XXIII—XXIII of the disposable diaper of FIG. 22.

Here, FIG. 22 is a perspective view showing the tenth embodiment of the present invention, and FIG. 23 is a sectional view taken on line XXIII—XXIII of a disposable diaper shown in FIGS. 22.

In the description to follow, the same points as the above-mentioned first and fifth embodiments, reference numerals between 200 to 300 are assigned and description thereof is omitted. With respect to those points not particularly described in detail, the description made in the description on the first to fifth embodiments is applicable, where appropriate.

A disposable diaper 201 according to the tenth embodiment shown in FIGS. 22 and 23 comprises a diaper body 230 including a topsheet 202, liquid-impermeable backsheet 203, an absorbent member (not shown) interposed therebetween, and one pair of left and right waist belt portions 240 for connecting a front body (stomach side portion B) and a back body (back side portion A) of the diaper body 230 together, the waist belt portion 240 comprising an inner surface sheet 241 located at an innermost position, the outermost layer sheet 207 located at an outermost position, and an intermediate sheet 242 located between the inner surface sheet 241 and the outermost layer sheet 207, and a waist-surrounding elastic member 213 fixedly held between the inner surface sheet 241 and the intermediate sheet 242, the intermediate sheet 242 and the outermost layer sheet 207 being not bonded together, and no gathers being formed on the outermost layer sheet 207.

More specifically, the diaper body 230 is not particularly limited in construction inasmuch as it comprises the topsheet 202, the backsheet 203, and the absorbent member interposed therebetween. In this embodiment, the diaper body 230 comprises the topsheet 202, the backsheet 203, and the absorbent member, longitudinal opposite end edge portions thereof being reduced in width in a forward direction.

As shown in FIG. 23, in the waist belt portion 240, the inner surface sheet 241 and the intermediate sheet 242 are generally the same in size, and fixedly hold the waist surrounding elastic member 213 therebetween. The outermost layer sheet 207 is located on an outer surface side of the intermediate sheet 242. Opposite side edge portions of the outermost layer sheet 207 are folded back to the inner surface sheet 241 side, and the folded back portions are firmly secured to an inner surface of the inner surface sheet 241. The outermost layer sheet 207 is not bonded to the intermediate sheet 242. Owing to this arrangement, a non-bonding area F is provided between the waist-surrounding elastic member 213 and the outermost layer sheet 207, so that no gathers are formed on an outer surface of the disposable diaper.

As the material for forming the inner surface sheet and the intermediate sheet, a nonwoven fabric, or plastic film such as polyethylene, urethane, or the like, and a lamination thereof which, are manufactured by various kinds of methods and usually used as sanitary material can be used.

Many changes and modifications can also be made in the tenth embodiment without departing from the gist of the present invention. For example, it is acceptable that the absorbent member is formed in a rectangular configuration, and an annular waist belt is used instead of the above-mentioned one pair of left and right waist belts:

What is claimed is:

1. A disposable wearing article comprising:

a liquid-permeable topsheet;

an outermost layer sheet;

a liquid retentive absorbent member;

a waist portion elastic member arranged at a waist opening portion, said waist opening portion being located at a waist edge of said disposable wearing article; and a waist-surrounding elastic member arranged at a waist-surrounding portion, said waist-surrounding portion being located adjacent said waist opening portion said waist-surrounding elastic member being fixed to members other than said outermost layer sheet in an expanded state to thereby form gathers inwardly of said outermost layer sheet;

wherein a non-bonding area is provided between said waist-surrounding elastic member and said outermost layer sheet, and no gathers are formed on an outer surface of said waist-surrounding portion.

2. A disposable wearing article comprising:

a liquid-permeable top sheet;

a liquid-impermeable backsheet;

an elastic member fixing sheet;

an inner layer sheet;

said absorbent member being interposed between said topsheet and said backsheet, said elastic member fixing sheet being disposed on an inner surface side of said backsheet, said inner layer sheet on which said absorbent member is placed being disposed on an inner surface side of said backsheet;

an outermost layer sheet;

a liquid retentive absorbent member;

a waist-surrounding elastic member arranged at a waist-surrounding portion, said waist-surrounding elastic member being fixed to members other than said outermost layer sheet in an expanded state to thereby form gathers inwardly of said outermost layer sheet;

said waist-surrounding elastic member being fixedly held between said inner layer sheet and said elastic member fixing sheet;

said backsheet not being bonded to a sheet located immediate to an inner surface thereof at an area where said waist-surrounding elastic member is present; and wherein a non-bonding area is provided between said waistsurrounding elastic member and said outermost layer sheet, and no gathers are formed on an outer surface of said waist-surrounding portion.

3. A disposable wearing article according to claim 1 further comprising a liquid-impermeable backsheet and an inner layer sheet, said absorbent member being interposed between said topsheet and said backsheet, said inner layer sheet on which said absorbent member is placed being disposed on an inner surface side of said backsheet, and said waist-surrounding elastic member being disposed on an inner surface side of said backsheet.

4. A disposable wearing article according to claim 1 further comprising a liquid-impermeable backsheet and an outer layer sheet;

said absorbent member being interposed between said topsheet and said backsheet;

said outer layer sheet being disposed between said backsheet and said outermost layer sheet; and said waist-surrounding elastic member being firmly secured, directly or through another sheet to said outer layer sheet.

5. A disposable wearing article according to claim 1, further comprising a diaper body including said topsheet, a liquid-impermeable backsheet, and said absorbent member interposed therebetween, and one pair of left and right waist belt portions for connecting a front body and a back body of said diaper body together; and said waist belt portions each comprising an inner surface sheet located in an innermost position, said outermost layer sheet located in an outermost position, an intermediate sheet located between said inner surface sheet and said outermost layer sheet, and a waist-surrounding elastic member firmly fixedly held between said inner surface sheet and said intermediate sheet, said intermediate sheet and said outermost layer sheet not being [not] bonded together, and no gathers being formed on said outermost layer sheet.

6. The disposable wearing article according to claim 1, wherein the waist portion elastic member is located and fixed between the outermost layer sheet and an inner layer sheet.

7. The disposable wearing article according to claim 1, wherein said waist portion elastic member is located outside of an edge of said liquid retentive absorbent member such that said liquid retentive absorbent member and said waist portion elastic member are arranged in non-overlapping manner.

8. The disposable wearing article according to claim 1, wherein said waist-surrounding elastic member entirely surrounds a waist of a wearer when in use.

9. The disposable wearing article according to claim 1, wherein said waist-surrounding portion is located immediately below said waist opening portion.

* * * * *